United States Patent [19]

Lundell et al.

[11] Patent Number: 5,048,341
[45] Date of Patent: Sep. 17, 1991

[54] CONTAINER WALL MEASURING APPARATUS AND METHOD

[75] Inventors: Dennis A. Lundell, Uniontown; Richard B. Nash, Cuyahoga Falls; James D. Stokes, Akron, all of Ohio

[73] Assignee: The Goodyear Tire & Rubber Company, Akron, Ohio

[21] Appl. No.: 459,690

[22] Filed: Jan. 2, 1990

[51] Int. Cl.$^5$ .................................. G01N 29/00
[52] U.S. Cl. .................................. 73/620; 73/146; 33/610
[58] Field of Search ............... 73/146, 597, 620, 622; 367/87; 33/783, 600, 610

[56] References Cited

U.S. PATENT DOCUMENTS

| | | | |
|---|---|---|---|
| 3,336,794 | 8/1967 | Wysoczanski et al. | 73/600 |
| 3,675,375 | 7/1972 | Enabnit et al. | 51/106 R |
| 3,762,056 | 10/1973 | Wolfe | 33/549 |
| 3,882,717 | 5/1975 | McCauley | 73/600 |
| 3,987,672 | 10/1976 | Loyer | 73/146 |
| 4,018,082 | 4/1977 | Manoliu et al. | 73/600 |
| 4,327,579 | 5/1982 | Weiss | 73/146 |
| 4,800,757 | 1/1989 | Hashinoki et al. | 73/597 |
| 4,936,138 | 6/1990 | Cushman et al. | 73/146 |

*Primary Examiner*—Hezron E. Williams
*Assistant Examiner*—Craig Miller
*Attorney, Agent, or Firm*—Frederick K. Lacher; T. P. Lewandowski

[57] ABSTRACT

A round open end container is supported and held on a turntable by a chuck. The edge of the container is guided and supported by rollers on roller heads mounted on brackets of stanchions positioned on opposite sides of the container. The brackets are movable vertically on the stanchions and the stanchions are movable radially relative to the turntable for positioning the rollers in supporting engagement with the edge of the container. A robot arm carries a C-shaped frame with opposing arms movable over the edge of the container between the rollers. Non-contact sensors are mounted on the arms of the C-shaped frame and are movable with the arms to predetermined vertical positions on opposite sides of the container wall for measuring the thickness of the wall at predetermined positions provided by rotation of the turntable.

10 Claims, 11 Drawing Sheets

CONTAINER WALL MEASURING APPARATUS AND METHOD

This invention relates generally to the measurement of the thickness of the wall of an open end container such as a tire or a bladder used for vulcanizing tires. It is important that the wall thickness of a bladder be molded in accordance with predetermined specifications so that the tires which are vulcanized are not distorted by the bladder.

Heretofore bladders were cut and the thickness of the wall measured by calipers. This system required destruction of the bladder and the manual measurement of the wall thickness. Not only was this a slow method but it did not indicate problems with the bladder mold in time to correct the problems and avoid molding a substantial number of defective bladders.

The present invention is directed to measuring the thickness of a bladder automatically by mounting the bladder on a turntable and adjusting the roller guides to support the edge of the bladder. A robot arm is then manipulated to carry non-contact sensors such as ultra sound sensors or laser heads mounted on a C-shaped frame into predetermined positions on opposite sides of the bladder wall for measuring the thickness of the wall. The turntable is rotated and the C-shaped frame is manipulated so that the thickness of the bladder can be measured at numerous circumferential and axial positions of the bladder. These measurements are transmitted to a computer where they are compared with the thickness of the wall as designed for that particular bladder. The difference between the actual and design thickness is then recorded for the predetermined positions. This information can then be studied with relation to the bladder mold and changes in the mold made to correct any problems. The turntable has a chuck with expandable clamps for gripping an edge of a bladder open at both ends. This chuck may be replaced by a contoured hub with passages leading to a source of vacuum for holding a bladder with a closed end and a concave center recess on the turntable. The roller heads for supporting the guide rollers engageable with the upper edge of the bladder may be rotated between two positions so that two sets of rollers can be utilized for engaging the inner surface of the bladder edge, depending upon the type of bladder being handled.

In accordance with one aspect of the invention there is provided an apparatus for measuring the thickness of a wall of a round container having at least one open end and a container axis comprising:

(a) turntable means for supporting the round container with the container axis coaxial with an axis of the turntable;

(b) guide roller means for placing inside an open end of the container for guiding edges of the container at the open end;

(c) frame means having opposing arms with measuring means mounted on the arms;

(d) frame supporting means for moving the frame means to a first circumferential position with the measuring means on opposite sides of a wall of the container at a first height over the turntable means;

(e) means for rotating the turntable means to predetermined circumferential positions at the first height for measuring the distance between the measuring means and the wall to determine the thickness of the wall at the circumferential positions at the first height;

(f) means for moving the frame means to a second height above the turntable means for measuring the distances of the measuring means from the wall to determine the thickness of the wall at the circumferential positions at the second height; and (g) means for retracting the guide roller means and the frame means from the round container so that the container can be removed from the turntable means.

In accordance with another aspect of the invention there is provided a method of measuring the wall thickness of a round container having at least one open end and a container axis comprising:

(a) placing the container on a turntable means with the container axis coaxial with an axis of the turntable means and an open end at an opposite end of the container from the turntable means;

(b) positioning guide roller means at the open end of the container for guiding an edge of the container at the open end;

(c) supporting a pair of non-contact distance measuring means on opposing spaced-apart arms of a frame means;

(d) moving the frame means to a first position with the measuring means on opposite sides of a wall of the container at a first height above the turntable means;

(e) measuring the distances of the measuring means from the wall to determine the thickness of the wall at the first position at the first height;

(f) rotating the turntable means through predetermined angles to a plurality of predetermined circumferential positions spaced from the first position at the first height and measuring the distances of the measuring means from the will to determine the thickness of the wall at the circumferential positions;

(g) moving the frame means to a predetermined second position at a second height over the turntable means;

(h) rotating the turntable means through predetermined angles to a plurality of predetermined circumferential positions spaced from the second position at the second height and measuring the distances of the measuring means from the wall to determine the thickness of the wall at the circumferential positions at the second height;

(i) retracting the guide rollers and the C-shaped frame from the round container and removing the round container from the turntable means.

To acquaint persons skilled in the arts most closely related to the present invention, a certain preferred embodiment thereof illustrating a best mode now contemplated for putting the invention into practice is described herein by and with reference to the annexed drawings forming a part of the specification. The embodiment shown and described herein is illustrative and as will become apparent to those skilled in these arts can be modified in numerous ways within the spirit and scope of the invention defined in the claims hereof.

Figure 1:
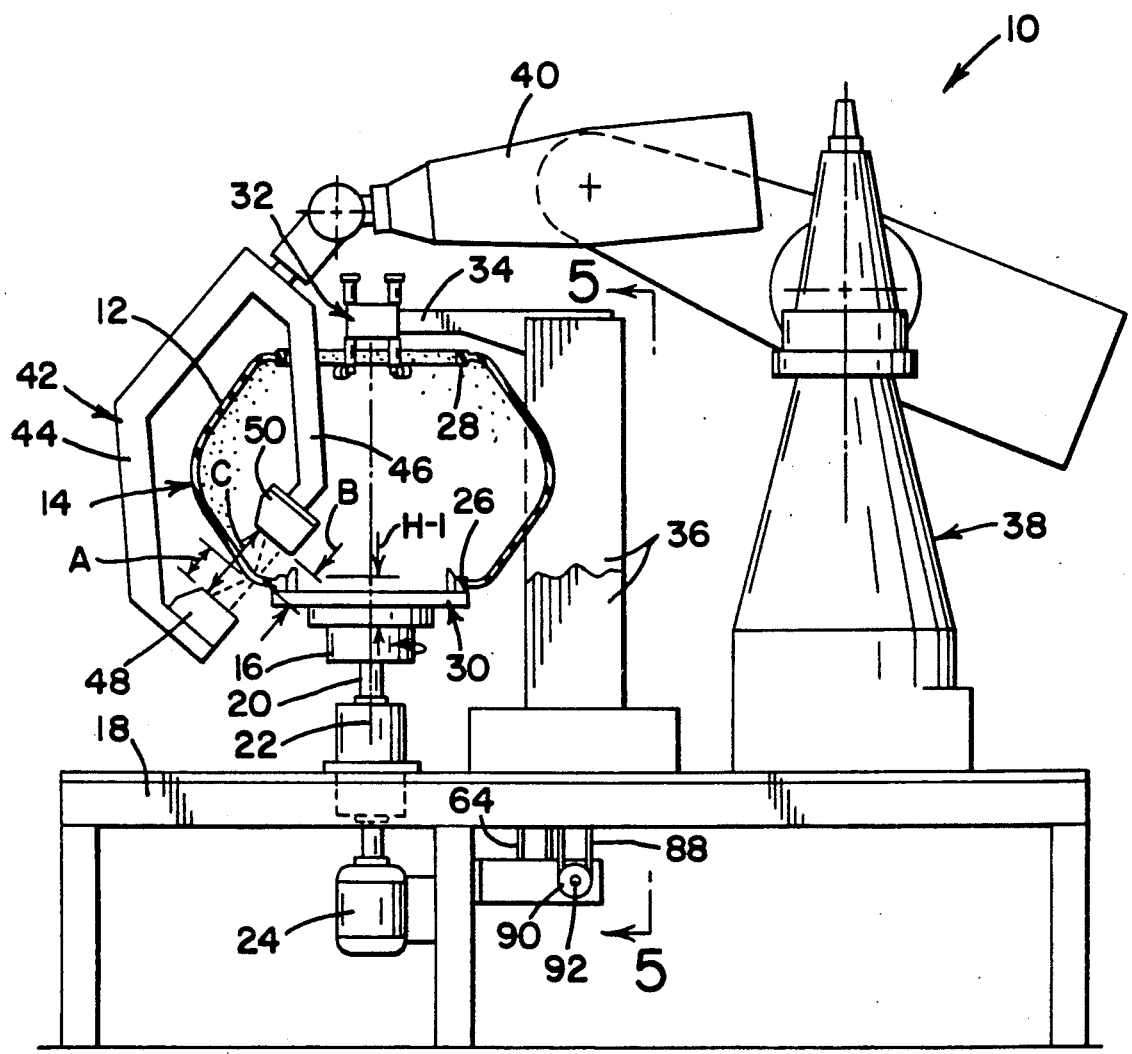
FIG. 1 is a schematic side elevation of the wall measuring apparatus embodying the invention as applied to a tire vulcanizer bladder showing the C-shaped frame on the robot arm in a first position with parts being broken away.

Referring to FIG. 1, a container wall measuring apparatus 10 is shown for measuring the thickness of a wall 12 of a round container such as a bladder 14 for a tire vulcanizer. The bladder 14 is mounted on a turntable 16 supported on a base 18 and having a shaft 20 for rotating the turntable about a turntable axis 22. The shaft 20 may be rotated in predetermined increments by a stepper motor 24 mounted on the base 18.

The bladder 14 has open ends with a lower edge such as lower bead 26 and an upper edge such as upper bead 28. The lower bead 26 may be gripped by a chuck 30 mounted on the turntable 16. The upper bead 28 may be supported by a pair of roller heads 32 mounted on roller support brackets 34 carried by stanchions 36 supported on the base 18. The stanchions are adjustably mounted on the base 18 for movement in a direction parallel to a diameter of the turntable 16 so as to move the brackets 34 together or apart and thereby move the roller heads 32 into or out of engagement with the upper bead 28. The brackets 34 are also adjustable vertically on the stanchions 36 in a direction parallel to the turntable axis 22 for positioning the roller heads 12 at the desired height to engage the upper bead 28 and for removing the roller heads from the bladder 14.

Figure 2:
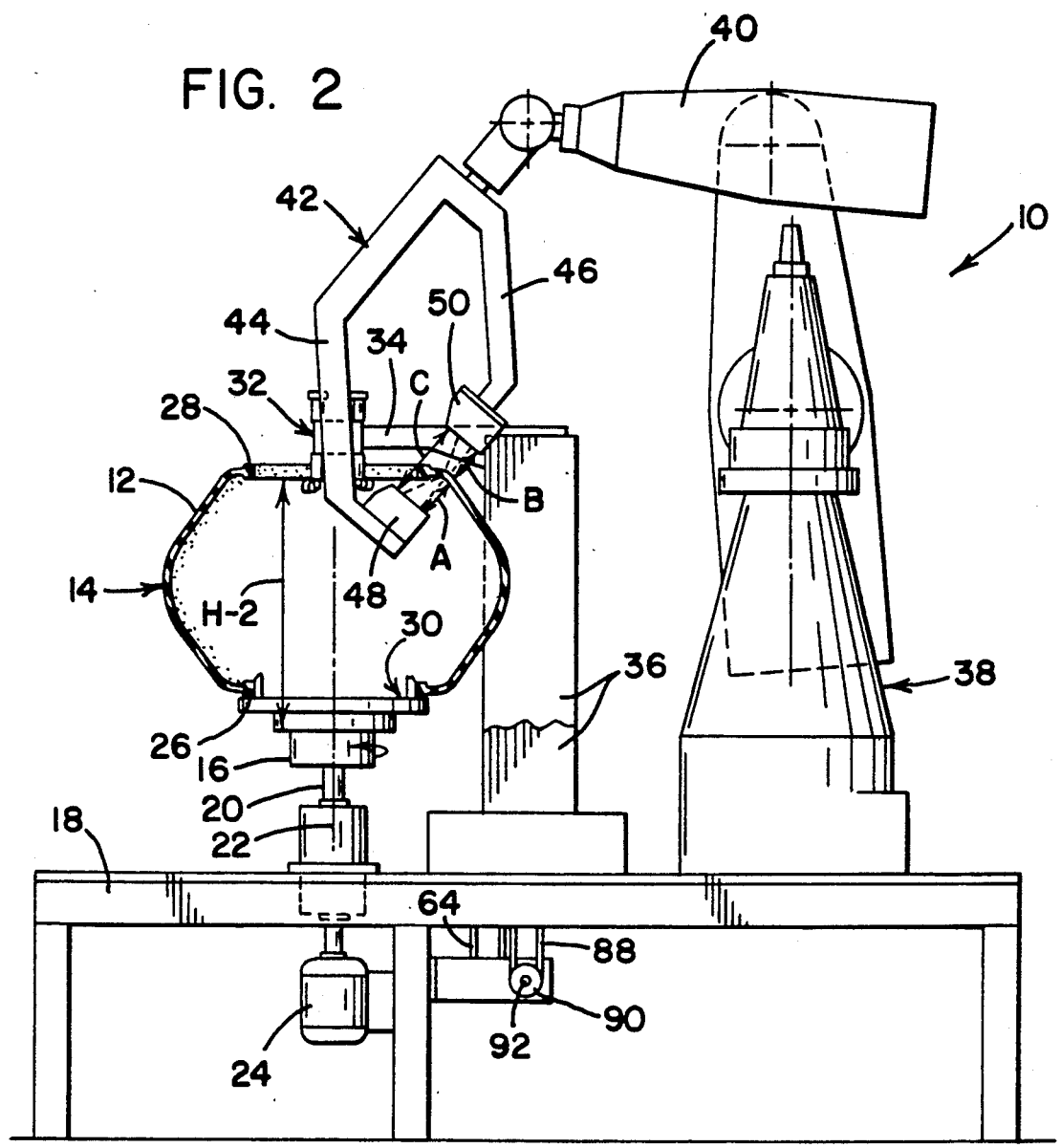
FIG. 2 is a view like FIG. 1 showing the C-shaped frame in position for measuring the wall thickness at a different height.
Figure 3:
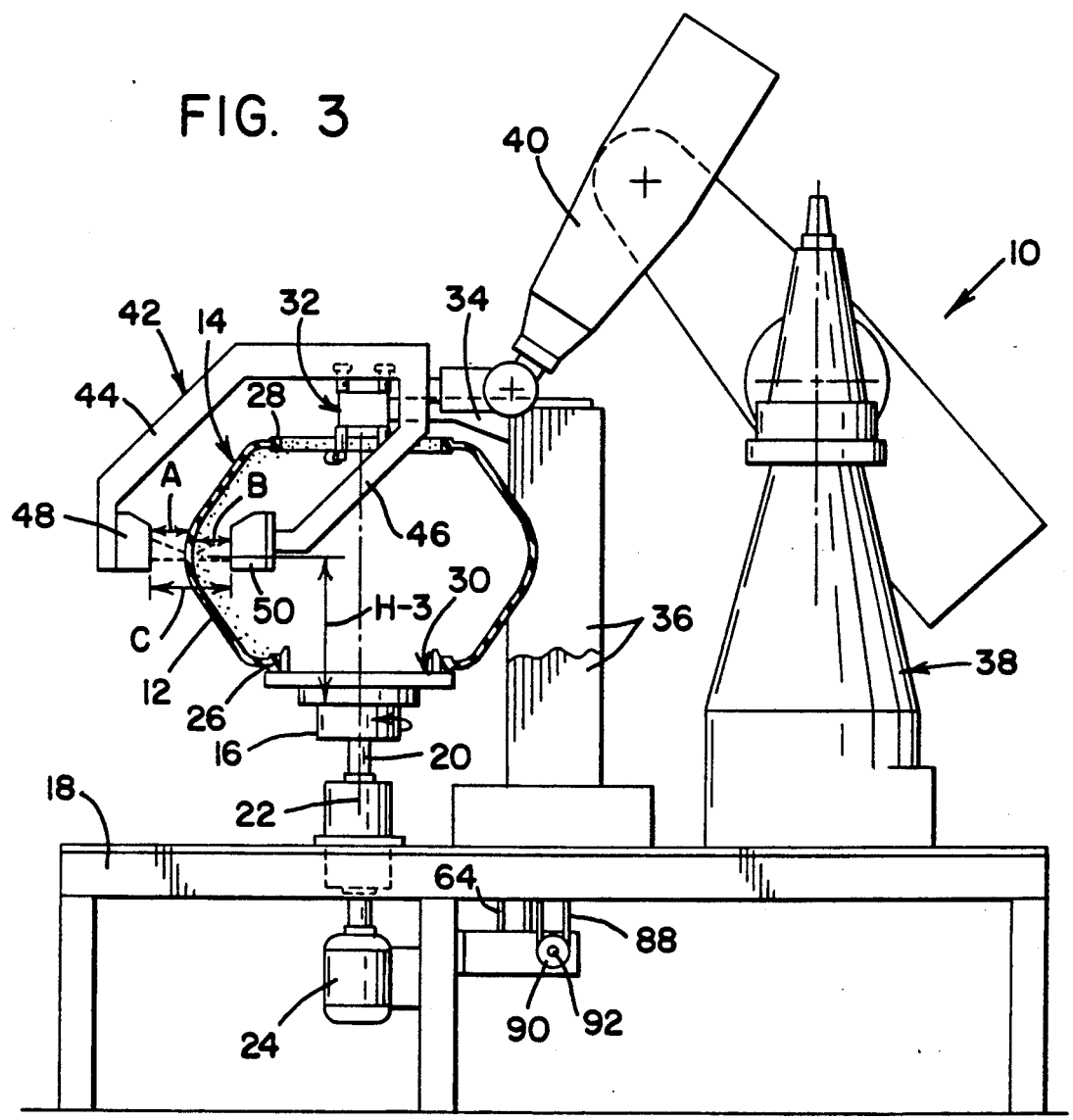
FIG. 3 is a view like FIGS. 1 and 2 showing the C-shaped frame in a third position for measuring the wall thickness at a still different height.

A robot 38 is mounted on the base 18 and has an articulated robot arm 40 which may be in three sections. A C-shaped frame member such as measuring frame 42 is mounted on the robot arm 40 and as shown in FIGS. 1, 2 and 3 may be moved to various positions by the robot arm. The measuring frame 42 has opposing arms 44 and 46 with non-contact thickness measuring means such as laser heads 48 and 50, respectively, mounted on the ends of the arms for measuring the distance A between the laser head 48 and the opposing surface of the wall 14 and the distance B between the laser head 50 and the opposing surface of the wall. In FIGS. 1 and 3, the laser head 48 is outside the bladder 14 and the laser head 50 is inside the bladder. In the position of the measuring frame 42 in FIG. 2, the laser head 48 is inside the bladder 14 and the laser head 50 is outside the bladder. The measuring frame 42 extends between the roller heads 32 and is movable for measuring the thickness of the wall at different heights H-1, H-2 and H-3 above the turntable 16 as shown in FIGS. 1, 2, and 3. In measuring the thickness of the wall 12, the distances A and B measured by the laser heads 48 and 50 are subtracted by a computer (not shown) from a known distance C between the laser head 48 and laser head 50 to obtain the thickness measurement. It is understood that other non-contact sensors such as ultra-sonic sensors may be used as an alternative to the laser heads 48 and 50.

The container wall measuring apparatus 10, shown in FIGS. 1, 2 and 3, may be enclosed with a fencing material and gate (not shown) to protect operators while the apparatus is in operation.

Figure 4:
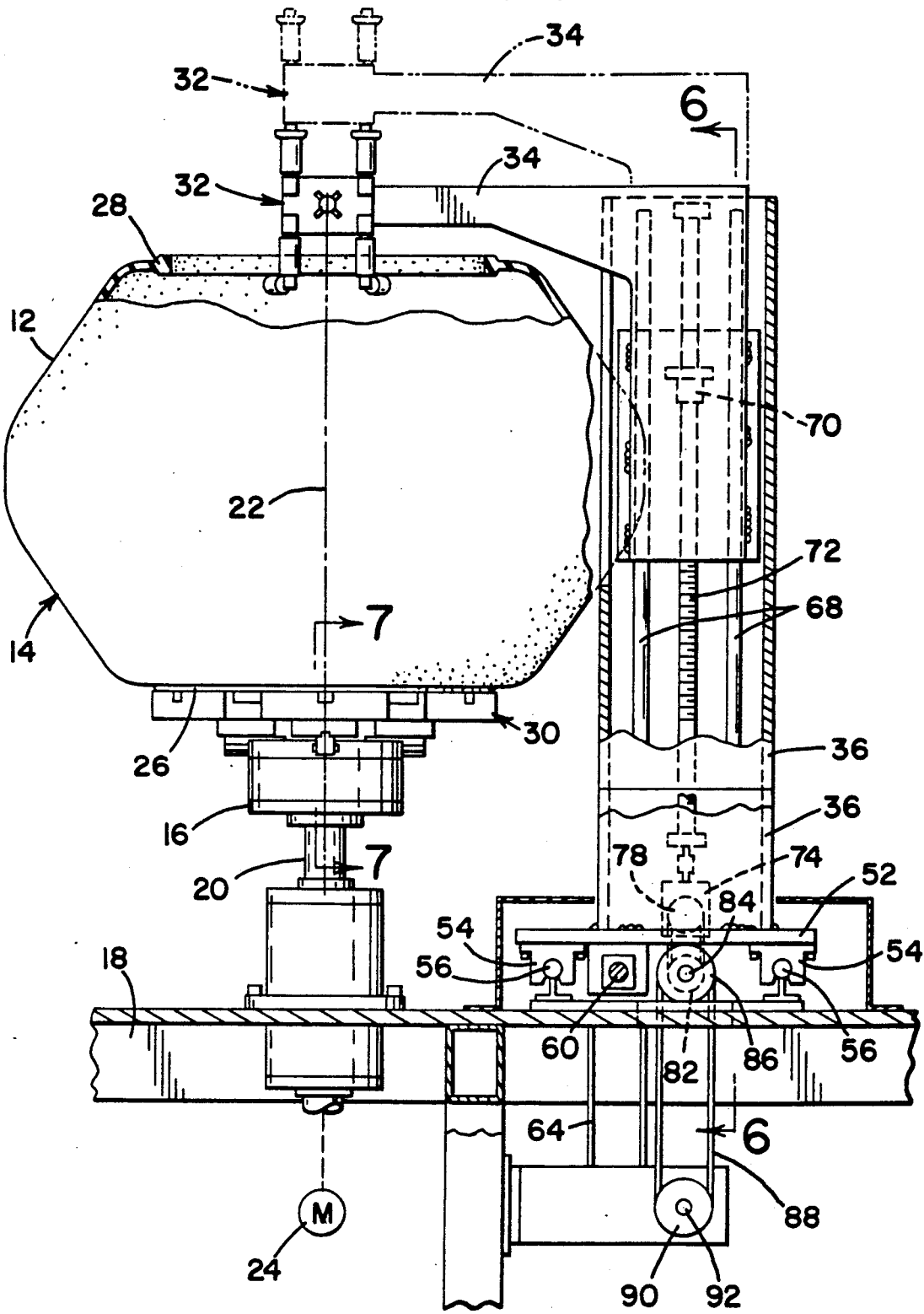
FIG. 4 is an enlarged detailed side elevation of the apparatus shown in FIGS. 1 through 3 with parts being broken away to show the drive mechanism for moving the roller heads into supporting relationship with the upper edge of the bladder.
Figure 5:
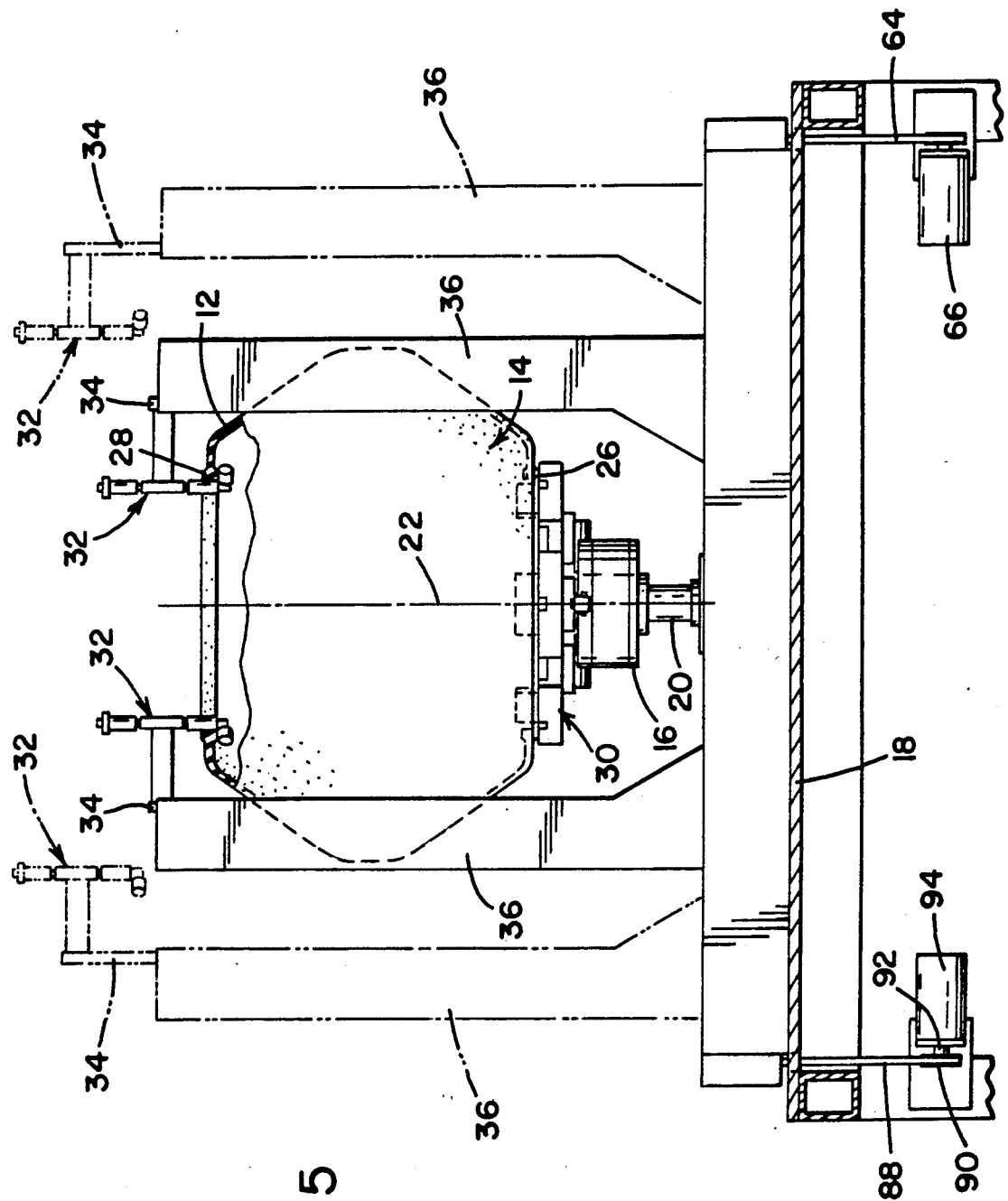
FIG. 5 is a schematic rear elevation taken along the plane of line 5-5 in FIG. 1 with parts being broken away and the stanchions shown in the retracted position in phantom lines.
Figure 6:
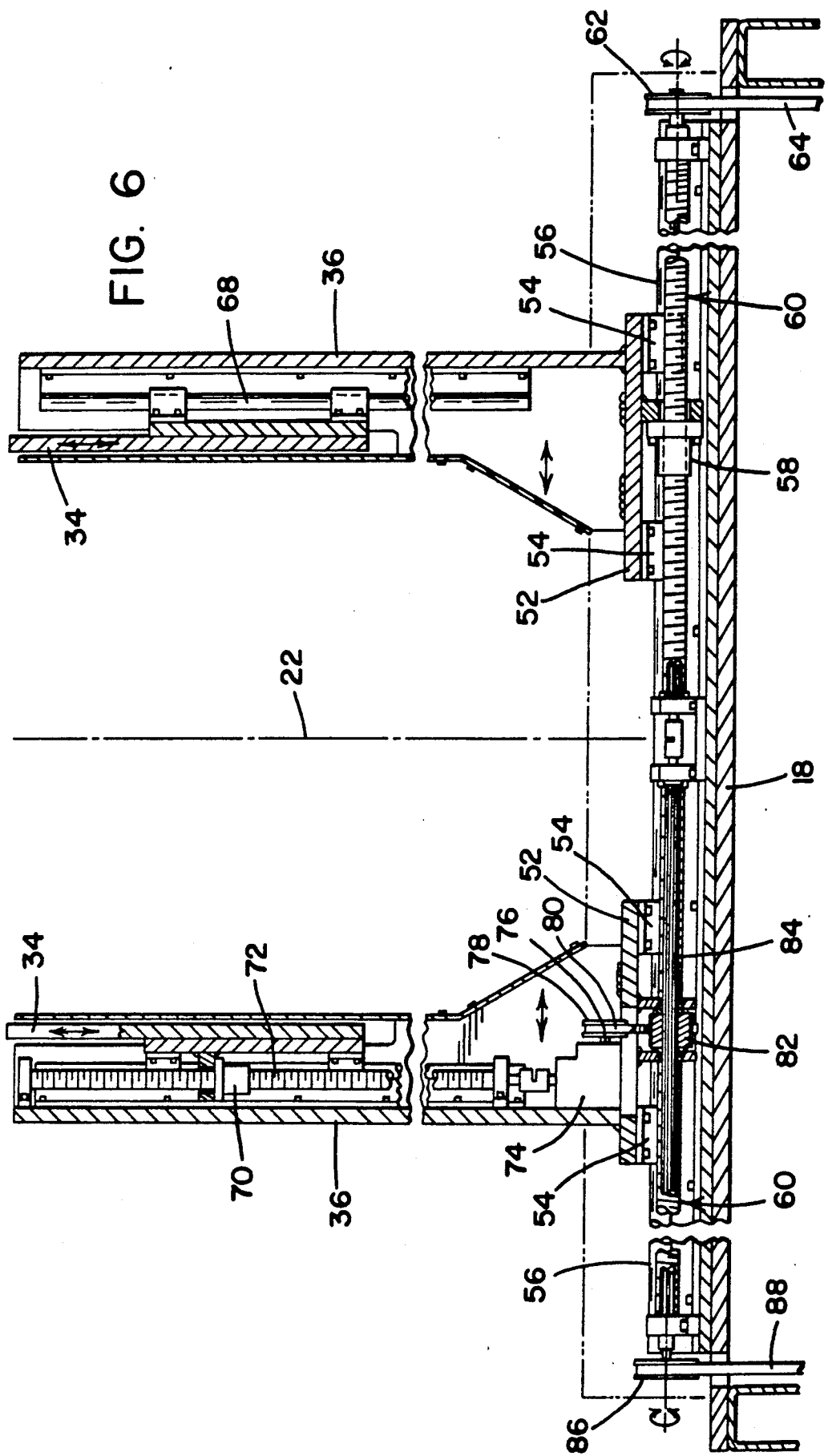
FIG. 6 is a sectional view taken along line 6—6 in FIG. 4 with parts being broken away.

Referring to FIGS. 4, 5 and 6, a more detailed illustration of the roller heads 32, roller support brackets 34 and stanchions 36 is shown.

Each of the stanchions 36 is mounted on a plate 52 having shoes 54 slidably mounted on rails 56 fastened to the base 18 guiding the stanchions 36 for movement toward and away from the plane of the turntable axis 22 between the positions shown in solid lines and phantom lines in FIG. 5. Each of the plates 52 has a nut member 58 engageable with a left-hand/right-hand drive screw member 60 having a pulley 62 driven by a belt 64 connected to a stepper motor 66 for turning the drive screw member and causing the stanchions 36 to move together or apart.

As shown in FIGS. 4 and 6, each of the brackets 34 is slidably mounted on vertical rods 68 fastened to the stanchions 36. Each of the brackets has a nut member 70 in threaded engagement with a vertical screw 72 connected to a gear box 74 mounted on the plate 52 and having a driving shaft 76 with a pulley 78 connected by a belt 80 to a splined pulley 82 slidably mounted on a splined shaft 84 extending along the rails 56 to a pulley 86 which is connected by a belt 88 to a pulley 90 mounted on a shaft 92 connected to a stepper motor 94. It can be seen that upon rotation of the splined shaft 84 by the stepper motor 94, the vertical screw 72 may be rotated and move the nut member 70 supporting the roller support bracket 34 between the position shown in phantom lines and solid lines in FIG. 4. When the stanchions 36 are moved toward or away from the plane of the turntable axis 22, the splined pulley 82 will slide along the splined shaft 84. In this way, the stanchions 36 and brackets 34 can be moved between the position shown in phantom lines and solid lines in FIG. 5 by selective rotation of the stepper motors 94 and 66.

Figure 7:
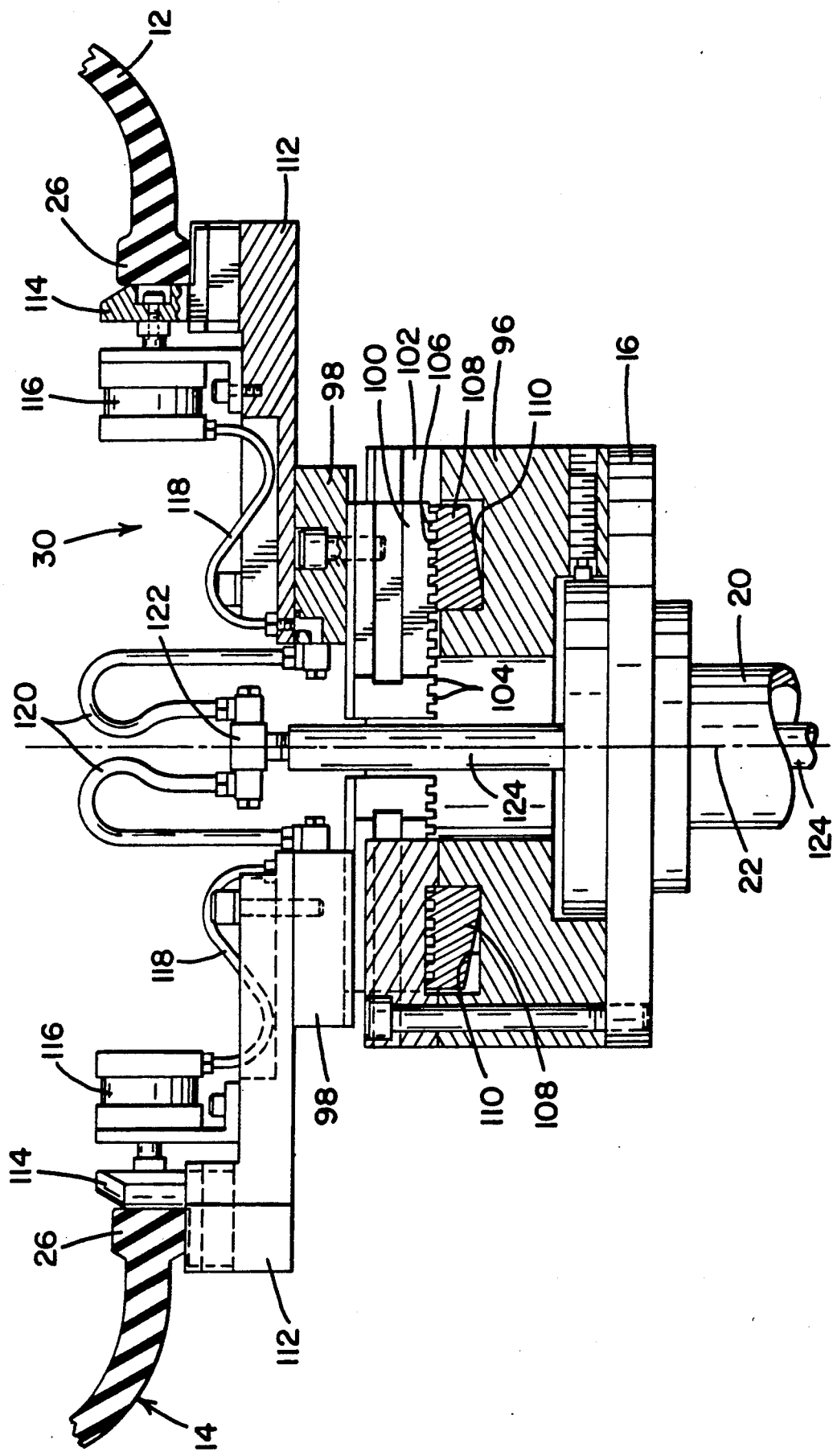
FIG. 7 is an enlarged fragmentary elevation in section of the turntable showing the chuck for gripping the edge of the bladder.
Figure 8:
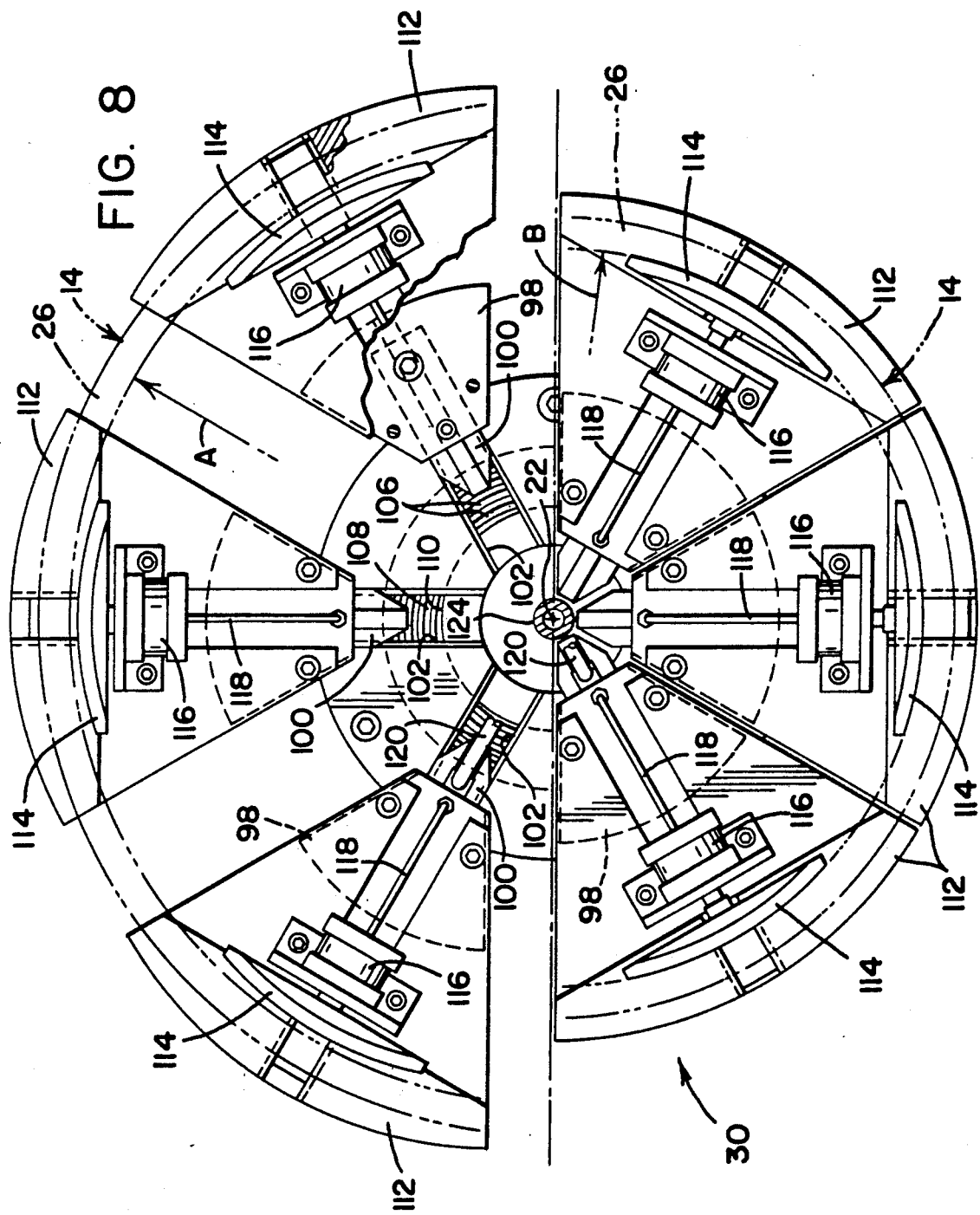
FIG. 8 is a plan view of the turntable and chuck shown in FIG. 7 showing some of the segments of the chuck in the expanded position.

Referring to FIGS. 7 and 8, the chuck 30 is shown in more detail. A hub 96 is mounted on the turntable 16 which is supported on the shaft 20. Mounted on the hub 96 are radially movable segments 98 having ribs 100 for seating in radially extending slots 102 in the hub. The ribs 100 may have teeth 104 for engagement with teeth 106 of keys 108 mounted in grooves 110 in the hub 96. Bladder supporting plates 112 are mounted on the segments 98 and have radially movable shoes 114 for engaging the lower bead 26 of the bladder 14. Piston and cylinder assemblies 116 may be mounted on the plates 112 for moving the shoes 114 radially into and out of engagement with the lower bead 26. Fluid pressure may be communicated to the piston and cylinder assemblies 116 by suitable hoses 118 and 120 connected to a manifold 122 supported on a pipe 124 extending through the center of the shaft 20 and leading to a suitable source of fluid pressure such as factory air (not shown).

This chuck 30 may be adjusted for clamping bladders 14 having different diameter lower beads 26 such as, for example, diameter A for the bladder shown in phantom lines in the upper part of FIG. 8 and diameter B for the bladder shown in the lower part of FIG. 8. This is accomplished by removing the segments 98 along with the ribs 100 and the plates 112 from the slots 102, disengaging the teeth 104 and 106. The segments 98, ribs 100 and plates 112 can then be moved radially to the desired position and the ribs 100 inserted in the slots 102 with the teeth 104 and 106 in engagement at that position. Then when the bladder 14 is placed on the plates 112, the shoes 114 can be moved radially a short distance into and out of engagement with the lower beads 26. The chuck 30 may also be used to clamp the lower beads of tires to be measured.

Figure 9:
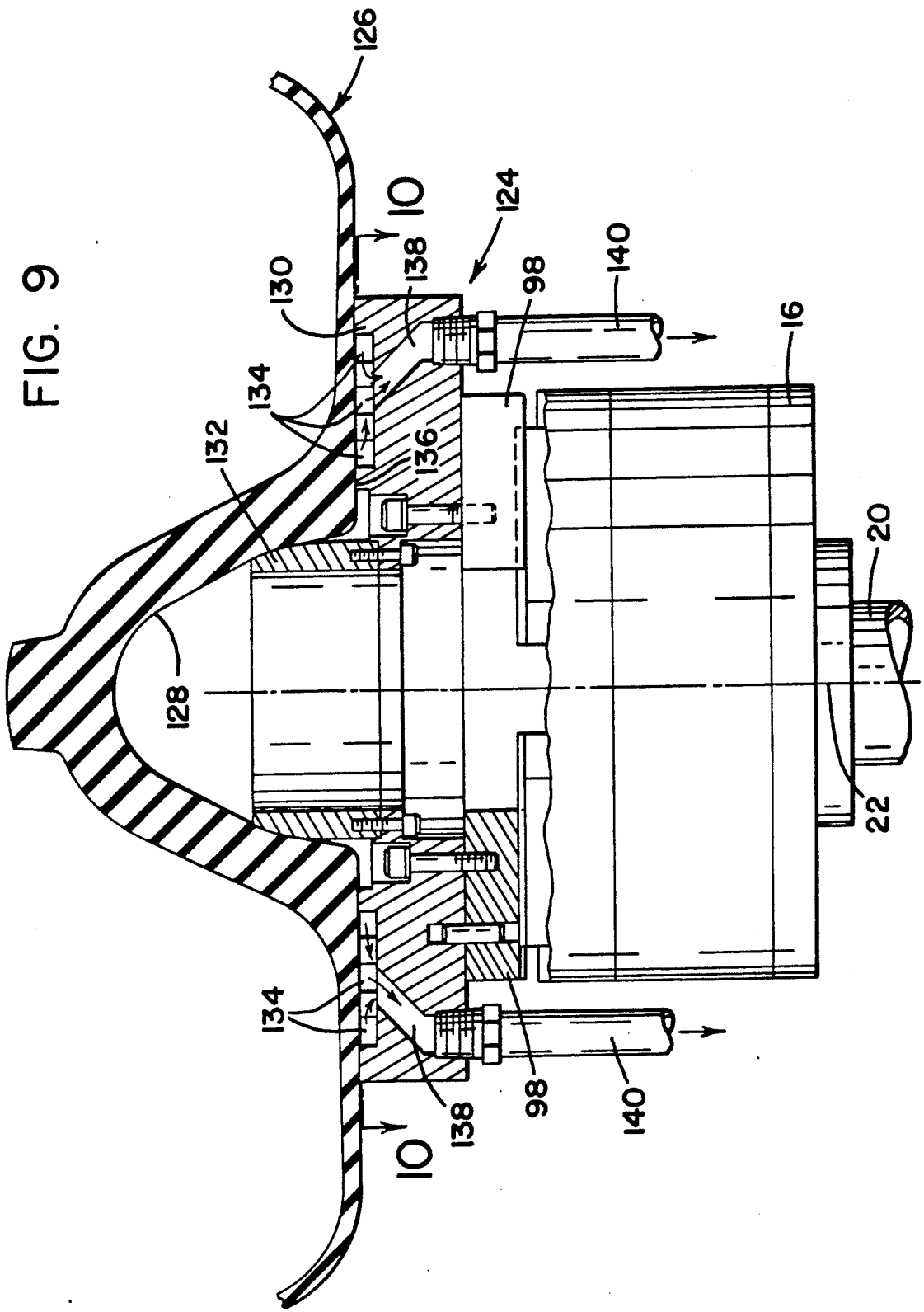
FIG. 9 is a fragmentary sectional view like FIG. 7 of a modified chuck for gripping a bladder with a closed end.
Figure 10:
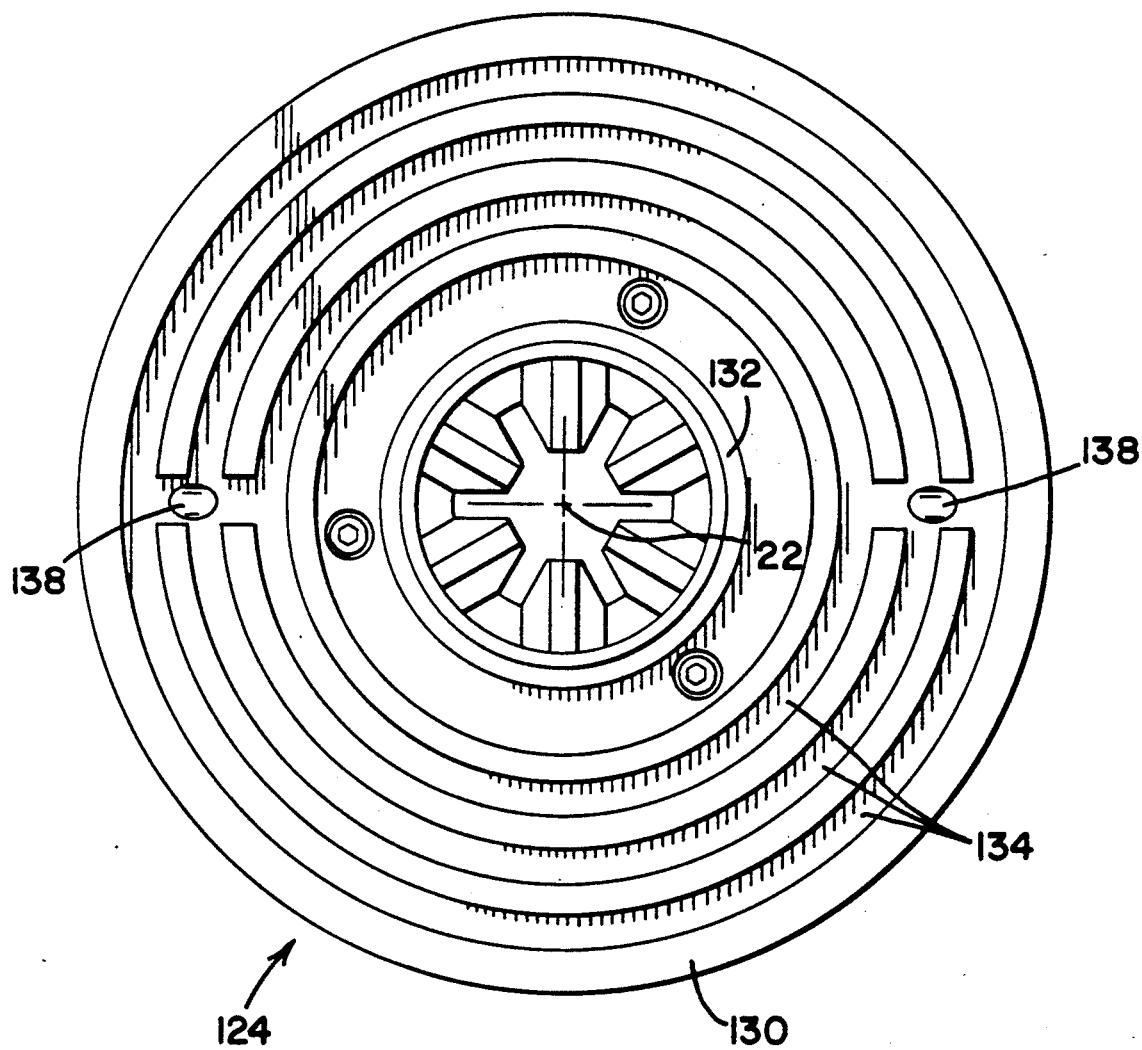
FIG. 10 is a plan view of the chuck taken along line 10—10 in FIG. 9.

Referring to FIGS. 9 and 10, a modified chuck 124 is shown for gripping a bladder 126 having a closed end with a concave center recess 128. The chuck 124 has a vacuum plate 130 mounted on the segments 98 of the chuck 30 shown in FIGS. 7 and 8. The plate 130 has a protruding hub 132 for engagement with the concave center recess 128. It also has concentric grooves 134 in the surface engageable with a flat bottom surface 136 of the bladder 126. The grooves 134 may be in communication with openings 138 connected to tubing 140 leading to a source of vacuum (not shown). When the bladder 126 is placed over the chuck 124, it will be centered on the protruding hub 132. Then when vacuum is communicated to the grooves 134, this will grip the bladder 126 and hold it on the turntable 16.

Figure 11:
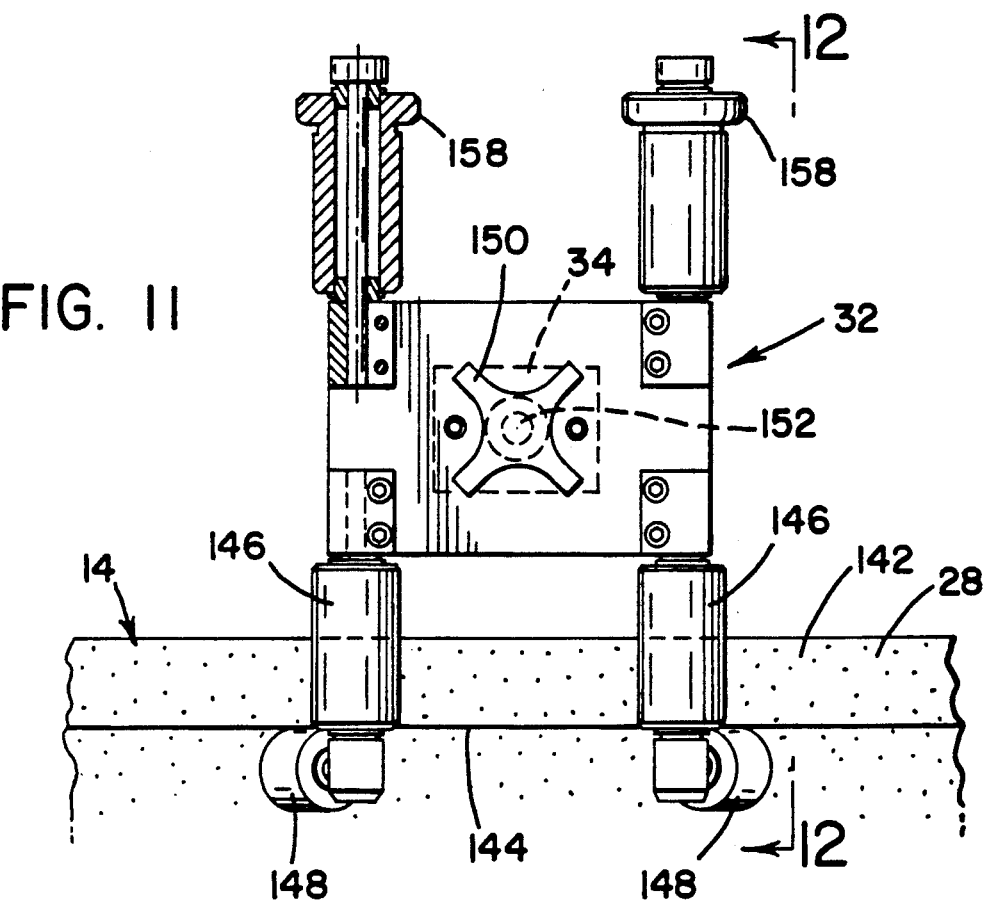
FIG. 11 is an enlarged fragmentary elevation, partly in section, of the roller head shown in FIG. 4 with the radially extending rollers positioned to engage an inside surface of the edge of the bladder.
Figure 12:
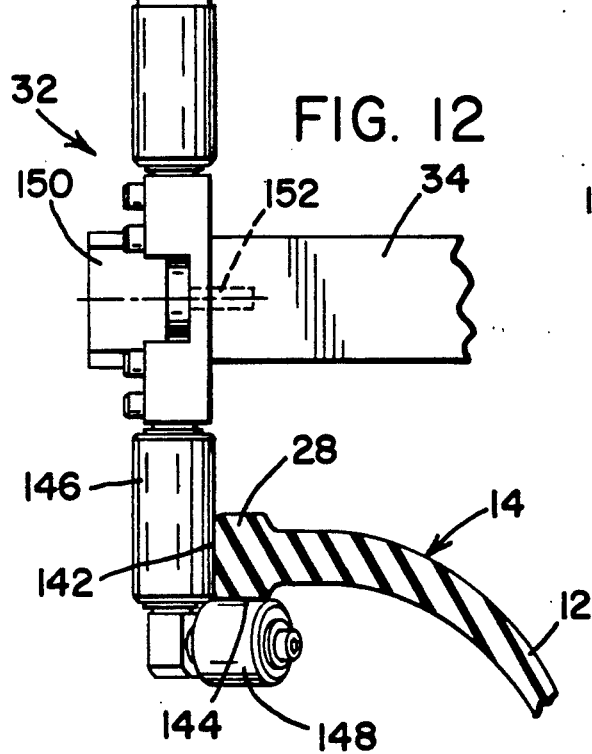
FIG. 12 is a fragmentary sectional view taken along line 12—12 in FIG. 11.
Figure 13:
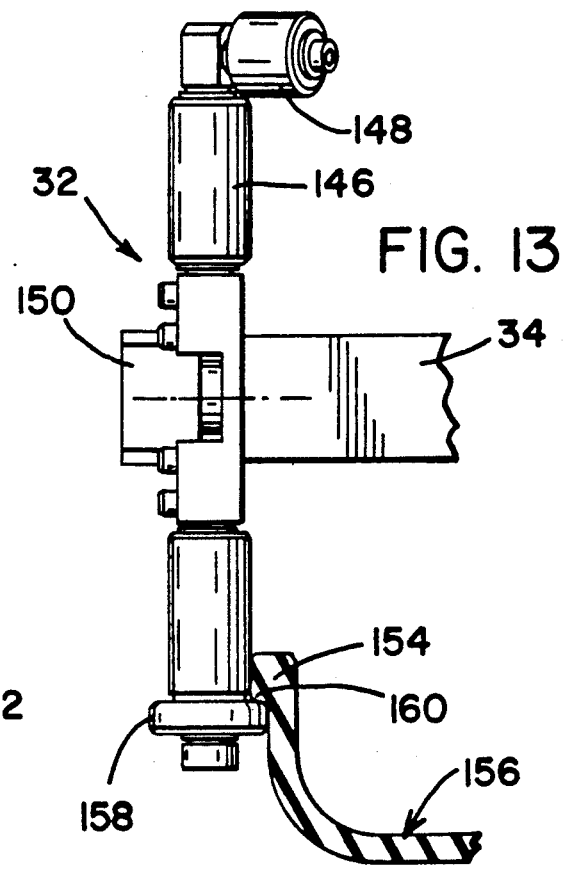
FIG. 13 is a fragmentary radial elevation like FIG. 12 showing the roller support rotated to position the axially extending rollers for engaging an inside surface of the edge of a different type bladder.

Referring to FIGS. 11, 12 and 13, one of the roller heads 32 is shown in greater detail. In FIGS. 11 and 12, the roller head 32 is in position for gripping an upper bead 28 of a bladder 14 shown in FIGS. 1 through 5. The upper bead 28 is gripped on an inside edge 152 and supported on a lower edge 144 by inside vertical rollers 146 and bottom rollers 148. The roller heads 32 are each mounted on one of the roller support brackets 34 by a hand knob 150 in threaded engagement with a threaded pivot rod 152 extending into the roller support bracket.

Referring to FIG. 13, one of the roller heads 32 is shown positioned for engaging an upper bead 154 of an alternate form of bladder 156. In this modification, a bottom roller 158 rotates about the same axis as the vertical roller 156 and has a greater diameter for engaging a lower shoulder 160 of the upper bead 154.

In operation, the operator sets the bladder 14 on the turntable 16 with the robot 38 in the position shown in FIG. 2 except that the arm 40 is rotated clockwise to move the measuring frame 42 to a position away from the space over the turntable. The operator then actuates the piston and cylinder assembly 116 of the chuck 30 to urge shoes 114 into engagement with the lower bead 26 of the bladder 14. Prior to setting the bladder 14 on the turntable 16 the operator can adjust the plates 112 for the diameter of the lower bead 26, as shown in FIG. 7.

The operator then actuates a roller support engage button of a suitable control mechanism to automatically adjust the roller heads 32 to support the upper bead 28 by movement of the stanchions 36 together and lowering of the brackets 34 to the desired height and then by movement of the stanchions apart until the roller heads 32 engage the upper bead. The operator then moves to a position outside the fencing material and gate enclosing the apparatus 10. In setting up the apparatus 10 the robot 38 is programmed for each bladder 14 with a teach pendant so that the robot will move the measuring frame 42 to the desired height H-1, H-2 and H-3 above the turntable 16. At each one of the heights H-1, H-2 and H-3, measurements of the thickness of the wall 12 are made by a laser system measuring the distances A and B between the laser heads 48 and 50 and the bladder 14. These measurements are made at predetermined positions as the turntable 16 is rotated by the stepper motor 24. Once a measurement is taken, the turntable 16 rotates to a new position and another reading is taken. This continues until the entire circumference has been measured at which point the robot 38 manipulates the measuring frame 42 so that the laser heads 46 and 48 measure a new point at a different height. When the entire bladder 14 has been gauged, the robot 38 removes the measuring frame 42 from the bladder and the area above the turntable 16. The operator then moves the stanchions 36 together and raises the brackets 34 to disengage the roller heads 32 from the upper bead 28 of the bladder 14 so that it can be manually removed from the turntable 16. The robot 38 and the laser heads 48 and 50 are connected to a computer which enters the data and indicates whether the bladder measured is acceptable. This data also indicates the uniformity of the bladder 14 and what needs to be done to the bladder mold if there is a problem.

While representative embodiments and details have been shown for the purpose of illustrating the invention, it will be apparent to those skilled in the art that various changes and modifications may be made therein without departing from the spirit or scope of the invention.

What is claimed is:

1. Apparatus for measuring the thickness of a wall of a round container having at least one open end and a container axis comprising:
    (a) turntable means for supporting said round container with said container axis coaxial with an axis of said turntable and including gripping means for holding said container on said turntable means;
    (b) guide roller means for placing inside an open end of said container for guiding edges of said container at said open end including a first roller head for positioning on one side of said container and a second roller head for positioning on an opposite side of said container;
    (c) frame means having opposing arms with measuring means mounted on said arms and movable into a measuring position between said first roller head and said second roller head;
    (d) frame supporting means for moving said frame means to a first circumferential position with said measuring means on opposite sides of a wall of said container at a first height over said turntable means;
    (e) means for rotating said turntable means to predetermined circumferential positions at said first height for measuring the distance between said measuring means and said wall to determine the thickness of said wall at said circumferential positions at said first height;
    (f) means for moving said frame means to a second height above said turntable means for measuring the distances of said measuring means from said wall to determine the thickness of said wall at said circumferential positions at said second height; and (g) means for retracting said guide roller means and said frame means from said round container so that said container can be removed from said turntable means.

2. The apparatus of claim 1 wherein said container has a closed end with a concave center recess for resting on said turntable means, said gripping means including a protruding hub on a supporting surface of said turntable means for centering engagement with said center recess and vacuum means in communication with said supporting surface for holding said closed end of said container on said turntable means.

3. The apparatus of claim 1 including adjusting means for moving said first roller head and said second roller head axially and radially of said turntable means into engagement with an edge of said container.

4. The apparatus of claim 3 wherein each said roller head is mounted on a roller support bracket axially adjustable on a roller support stanchion, each said roller support stanchion being adjustable in a direction parallel to a radius of said turntable means to provide radial adjustment of said roller head with said roller support bracket being movable in a direction parallel to said axis of said turntable means for moving said roller head into guiding engagement with said edge of said container.

5. The apparatus of claim 4 wherein each said roller support stanchion is slidably mounted on rail means and has a nut member engageable with a left-hand/right-hand drive screw member, said roller support bracket being raised and lowered by a screw member rotatable in response to rotation of a pulley member connected to a splined pulley by a belt, and drive means for rotating said splined pulley and said left-hand/right-hand screw member.

6. The apparatus of claim 5 including a splined shaft with said splined pulley being slidably mounted on said splined shaft and positioned adjacent to said rail means, and drive means connected to said splined shaft for rotating said splined shaft and said splined pulley to rotate said screw member and raise and lower said roller support bracket.

7. The apparatus of claim 1 wherein said frame means is a one piece C-shaped frame having opposing arms and said measuring means includes non-contact sensors mounted on said opposing arms and means for moving said opposing arms into positions on opposite sides of said wall for measuring the distance between each of said non-contact sensors and the surfaces of said wall located between said non-contact sensors.

8. The apparatus of claim 7 wherein said C-shaped frame is mounted on a robot arm of a robot apparatus, said robot arm being movable to provide axial movement of said C-shaped frame carrying said non-contact sensors to said positions on opposite sides of said wall.

9. A method of measuring the wall thickness of a round container having at least one open end of a container axis comprising:

(a) placing said container on a turntable means with said container axis coaxial with an axis of said turntable means and an open end at an opposite end of said container from said turntable means;

(b) positioning guide roller means at said open end of said container for guiding an edge of said container at said open end;

(c) supporting a pair of non-contact distance measuring means on opposing spaced-apart arms of a frame means;

(d) moving said frame means to a first position with said measuring means on opposite sides of a wall of said container at a first height above said turntable means;

(e) measuring the distances of said measuring means from said wall to determine the thickness of said wall at said first position at said first height;

(f) rotating said turntable means through predetermined angles to a plurality of predetermined circumferential positions spaced from said first position at said first height and measuring the distances of said measuring means from said wall to determine the thicknesses of said wall at said circumferential positions;

(g) moving said frame means to a predetermined second position at a second height over said turntable means;

(h) rotating said turntable means through predetermined angles to a plurality of predetermined circumferential positions spaced from said second position at said second height and measuring the distances of said measuring means from said wall to determine the thickness of said wall at said circumferential positions at said second height;

(i) holding said container on said turntable means by gripping means during said measuring of the distances of said measuring means from said wall and releasing said gripping means after said measuring is completed;

(j) retracting said guide rollers and said frame means from said round container and removing said round container from said turntable means.

10. The method of claim 9 wherein said frame means includes a one piece C-shaped frame and moving said frame means includes moving said frame to position one of said opposing arms inside said container and position the other of said opposing arms outside of said container.

* * * * *